United States Patent
Adair et al.

(10) Patent No.: US 11,472,786 B2
(45) Date of Patent: Oct. 18, 2022

(54) METHODS FOR CONVERTING THC-RICH CANNABINOID MIXTURES INTO CBN-RICH CANNABINOID MIXTURES

(71) Applicant: Canopy Growth Corporation, Smiths Falls (CA)

(72) Inventors: Christopher Adair, Smiths Falls (CA); Mahmood Azizpoor Fard, Smiths Falls (CA); Ben Geiling, Smiths Falls (CA); Mohammadmehdi Haghdoost Manjili, Smiths Falls (CA)

(73) Assignee: Canopy Growth Corporation, Smiths Falls (CA)

( * ) Notice: Subject to any disclaimer, the term of this patent is extended or adjusted under 35 U.S.C. 154(b) by 0 days.

(21) Appl. No.: 17/677,457

(22) Filed: Feb. 22, 2022

(65) Prior Publication Data

US 2022/0177442 A1 Jun. 9, 2022

Related U.S. Application Data

(63) Continuation of application No. PCT/CA2020/051146, filed on Aug. 21, 2020.

(60) Provisional application No. 62/891,038, filed on Aug. 23, 2019.

(51) Int. Cl.
*C07D 311/80* (2006.01)
*C07C 50/04* (2006.01)
*C07C 50/24* (2006.01)

(52) U.S. Cl.
CPC ............ *C07D 311/80* (2013.01); *C07C 50/04* (2013.01); *C07C 50/24* (2013.01)

(58) Field of Classification Search
CPC .................................................... C07D 311/80
See application file for complete search history.

(56) References Cited

U.S. PATENT DOCUMENTS

| 6,403,126 | B1 | 6/2002 | Webster et al. | |
| 8,497,299 | B2 * | 7/2013 | Mechoulam | A61K 31/352 514/454 |
| 2014/0248379 | A1 * | 9/2014 | Mueller | A61K 36/185 424/725 |
| 2014/0271940 | A1 | 9/2014 | Wurzer | |

FOREIGN PATENT DOCUMENTS

| EP | 3459536 A1 | 3/2019 |
| WO | WO 2017/214529 A1 | 12/2017 |
| WO | WO 2020/028992 A1 | 2/2020 |
| WO | WO 2020/101731 A1 | 5/2020 |

OTHER PUBLICATIONS

Pollastro et al. (J. Nat. Prod. 2018, 81, 630-633).*
Mechoulam (J. Am. Chem. Soc., 90(9), 2418, (1968)).*
Guo (J. Am. Chem. Soc. 2014, 136, 11499-11512)).*
Smith (March's Advanced Organic Chemistry: Reactions, Mechanisms, and Structure, 5th Edition (2001), p. 1510-1511).*
Wendlandt (Angew. Chem. Int. Ed. Engl. Dec. 1, 2015; 54(49):14638-14658).*
Hollister et al., "Interactions in man of delta-9-tetrahydrocannabinol; II. Cannabinol and Cannabidiol", ASCPT—Clin Pharmacol Ther, 1975, 18(1): 80-83.
Husni AS et al., "Evaluation of phytocannabinoids from high-potency Cannabis sativa suing in vitro bioassays to determine structure-activity relationships for cannabinoid receptor 1 and cannabinoid receptor 2", Med Chem Res, 2014, 23(9): 4295-4300.
Huynh et al., "Quinone 1 e− and 2 e−/2 H+ Reduction Potentials: Identification and Analysis of Deviations from Systematic Scaling Relationships", J Am Chem Soc, 2016, 138(49): 15903-15910, S1-S34.
Mechoulam et al., "Cannabidiol: an overview of some chemical and pharmacological aspects. Part 1: chemical aspects", Chemistry and Physics of Lipids, 2002, 121: 35-43.
Mechoulam et al., "Stereoelectronic Factor in the Chloranil Dehydrogenation of Cannabinoids. Total Synthesis of dl-Cannabichromene", J Am Chem Soc 1968, 90(9): 2418-2420.
Morales, et al., "An Overview on Medicinal Chemistry of Synthetic and Natural Derivatives of Cannabidiol", Front Pharmacol, 2017, 8(422): 1-18.
Pollastro et al., "Iodine-Promoted Aromatization of p-Menthane-Type Phytocannabinoids", J Nat Prod, 2018, 81(3): 630-633, S1-S3.

* cited by examiner

*Primary Examiner* — Valerie Rodriguez-Garcia
(74) *Attorney, Agent, or Firm* — Knobbe Martens Olson & Bear LLP

(57) ABSTRACT

Disclosed herein is a method of converting a THC-rich cannabinoid mixture that comprises at least about 20% THC into a CBN-rich cannabinoid mixture that comprises at least about 2.0% CBN. The method comprises contacting the cannabinoid mixture with a benzoquinone reagent under reaction conditions comprising: (i) a reaction temperature that is within a target reaction-temperature range; and (ii) a reaction time that is within a target reaction-time range, such that at least a portion of the of the THC in the THC-rich cannabinoid mixture is converted into CBN.

19 Claims, No Drawings

METHODS FOR CONVERTING THC-RICH CANNABINOID MIXTURES INTO CBN-RICH CANNABINOID MIXTURES

CROSS-REFERENCE TO RELATED APPLICATIONS

This application is a continuation of International Application No. PCT/CA2020/051146, which is hereby incorporated by reference in its entirety, which claims priority to and benefit of U.S. Provisional Patent Application Ser. No. 62/891,038 filed on Aug. 23, 2019, which is hereby incorporated by reference in its entirety.

TECHNICAL FIELD

The present disclosure generally relates to methods for converting tetrahydrocannabinol (THC)-rich cannabinoid mixtures into cannabinol (CBN)-rich cannabinoid mixtures.

BACKGROUND

Cannabinol (CBN) is a well-known cannabinoid that is currently being investigated for a wide variety of therapies—at least in part due to its mild psychoactive effects and potential to act as an allosteric modulator of interactions between other cannabinoids and cannabinoid receptors. For the same reasons, CBN may be of interest to those developing recreational cannabinoid products. CBN may also have potential utility as a synthon for organic chemistry transformations. Accordingly, medicinal, recreational, and/or synthesis applications would benefit from simple, efficient methods of obtaining CBN. Unfortunately such methods are in short supply. Like many cannabinoids, CBN is typically sourced from biomass that comprises numerous cannabinoids and other components such as oils, waxes, alkaloids, and the like. Isolating CBN from such complex mixtures can be challenging—particularly because CBN is often present in low/trace quantities which may not be amenable to extraction.

SUMMARY

In view of the limited options for obtaining scalable quantities of cannabinol (CBN), the present disclosure provides methods of converting THC-rich cannabinoid mixtures into CBN-rich cannabinoid mixtures. Importantly, by utilizing a complex mixture of cannabinoids as an input material, the methods of the present disclosure obviate the need for expensive, hazardous, and/or time-consuming purification methods as precursors to the conversion of THC to CBN. Instead the methods of the present disclosure are adapted for use with THC-rich cannabinoid mixtures such as THC distillates, extracts, and the like. Such THC-rich cannabinoid mixtures are readily accessible, for example because a preponderance of methods have been developed to obtain THC-rich cannabinoid mixtures from a wide variety of biomass-derived cannabinoid sources.

The present disclosure reports that thymoquinone can be utilized to convert THC-rich cannabinoid mixtures into CBN-rich cannabinoid mixtures. Thymoquinone is a naturally occurring compound that is currently being investigated due to its potential activity as a hepatoprotective agent, an anti-inflammatory agent, an antioxidant, a cytotoxic agent, and/or an anti-cancer agent. In contrast to the active research in these areas, relatively little work has been done to elucidate how thymoquinone can be utilized in the *cannabis* space.

More generally, the present disclosure reports that a variety of benzoquinone reagents can be utilized to convert THC-rich cannabinoid mixtures into CBN-rich cannabinoid mixtures, and that various benzoquinone reagents can be utilized to execute such conversions with varying degrees of selectivity. Importantly, the experimental results reported herein indicate that benzoquinones can be used to convert THC-rich cannabinoid mixtures into CBN-rich cannabinoid mixtures under relatively mild reaction conditions without requiring harmful solvents such as benzene.

Select embodiments of the present disclosure relate to a method of converting a THC-rich cannabinoid mixture that comprises at least about 20% THC into a CBN-rich cannabinoid mixture that comprises at least about 2.0% CBN, the method comprising contacting the cannabinoid mixture with a benzoquinone reagent under reaction conditions comprising: (i) a reaction temperature that is within a target reaction-temperature range; and (ii) a reaction time that is within a target reaction-time range, such that at least a portion of the of the THC in the THC-rich cannabinoid mixture is converted into CBN.

Select embodiments of the present disclosure relate to a method of converting a THC-rich cannabinoid mixture that comprises at least about 75% THC into a CBN-rich cannabinoid mixture that comprises at least about 40% CBN, the method comprising contacting the cannabinoid mixture with tetrachloro-1,4-benzoquinone under reaction conditions comprising: (i) a reaction temperature that is within a target reaction-temperature range; and (ii) a reaction time that is within a target reaction-time range.

Select embodiments of the present disclosure relate to a method of converting a THC-rich cannabinoid mixture that comprises at least about 75% THC into a cannabinol CBN-rich cannabinoid mixture that comprises at least about 15% CBN, the method comprising contacting the cannabinoid mixture with 2-isopropyl-5-methyl-1,4-benzoquinone under reaction conditions comprising: (i) a reaction temperature that is within a target reaction-temperature range; and (ii) a reaction time that is within a target reaction-time range.

Other aspects and features of the methods of the present disclosure will become apparent to those ordinarily skilled in the art upon review of the following description of specific embodiments.

DETAILED DESCRIPTION

As noted above, the present disclosure reports that thymoquinone can be utilized to convert tetrahydrocannabinol (THC)-rich cannabinoid mixtures into cannabinol (CBN)-rich cannabinoid mixtures. More generally, the present disclosure reports that a variety of benzoquinone reagents are useful in this respect, and that such reagents show varying degrees of selectivity for THC over other cannabinoids in the mixture (such as cannabidiol (CBD)). Without being bound to any particular theory, the present disclosure posits that the ability of benzoquinone reagents to convert THC-rich cannabinoid mixtures into CBN-rich cannabinoid mixtures as set out herein may be tied to a combination of steric and electronic effects. For example, with respect to steric effects, experiments indicate that naphthoquinones and anthraquinones—which present substantially bulkier steric profiles relative to benzoquinones—are less effective under the conditions investigated, and with respect to electronic effects, experiments suggest that THC-conversion reactivity may correlate with oxidation potential under the conditions investigated. Importantly, the experimental results reported herein indicate that benzoquinones can be used to convert THC-rich cannabinoid mixtures to CBN-rich cannabinoid mixtures under relatively mild reaction conditions without requiring harmful solvents such as benzene.

In select embodiments, the present disclosure provides a method for converting THC-rich cannabinoid mixtures into mixtures of CBN and other cannabinoids. Select embodiments of the present disclosure relate to a method of converting a THC-rich cannabinoid mixture that comprises at least about 20% THC into a CBN-rich cannabinoid mixture that comprises at least about 2.0% CBN, the method comprising contacting the cannabinoid mixture with a benzoquinone reagent under reaction conditions comprising: (i) a reaction temperature that is within a target reaction-temperature range; and (ii) a reaction time that is within a target reaction-time range, such that at least a portion of the of the THC in the THC-rich cannabinoid mixture is converted into CBN.

In the context of the present disclosure, the term "contacting" and its derivatives is intended to refer to bringing the THC-rich cannabinoid mixture and the benzoquinone reagent as disclosed herein into proximity such that a chemical reaction can occur. In some embodiments of the present disclosure, the contacting may be by adding the benzoquinone reagent to the THC-rich cannabinoid mixture. In some embodiments, the contacting may be by combining, mixing, or both.

In select embodiments of the present disclosure, the THC-rich cannabinoid mixture may comprise: (i) at least about 40 wt. % THC; (ii) at least about 60 wt. % THC; (iii) at least about 80 wt. % THC; or (iv) at least about 95 wt. % THC.

In select embodiments of the present disclosure, the THC-rich cannabinoid mixture may comprise cannabidiol (CBD), and the THC content of the THC-rich cannabinoid mixture may be reduced to a greater extent than the CBD content of the THC-rich cannabinoid mixture on a weight-to-weight basis.

In select embodiments of the present disclosure, the CBN-rich cannabinoid mixture may have: (i) at least about 10 wt. % more CBN than the THC-rich cannabinoid mixture on a weight-to-weight basis; (ii) at least about 30 wt. % more CBN than the THC-rich cannabinoid mixture on a weight-to-weight basis; (iii) at least about 60 wt. % more CBN than the THC-rich cannabinoid mixture on a weight-to-weight basis; or (iv) at least about 90 wt. % more CBN than the THC-rich cannabinoid mixture on a weight-to-weight basis.

In select embodiments of the present disclosure, the THC-rich cannabinoid mixture may be derived from marijuana biomass. In select embodiments of the present disclosure, the THC-rich cannabinoid mixture may be a distillate, a resin, an extract, or a combination thereof.

In the context of the present disclosure, a "cannabinoid mixture" is any compositions that comprises at least two cannabinoids. As used herein, the term "cannabinoid" refers to: (i) a chemical compound belonging to a class of secondary compounds commonly found in plants of genus *cannabis*, (ii) synthetic cannabinoids and any enantiomers thereof; and/or (iii) one of a class of diverse chemical compounds that may act on cannabinoid receptors such as CB1 and CB2.

In select embodiments of the present disclosure, the cannabinoid is a compound found in a plant, e.g., a plant of genus *cannabis*, and is sometimes referred to as a phyto-cannabinoid. One of the most notable cannabinoids of the phytocannabinoids is tetrahydrocannabinol (THC), the primary psychoactive compound in *cannabis*. Cannabidiol (CBD) is another cannabinoid that is a major constituent of the phytocannabinoids. There are at least 113 different cannabinoids isolated from *cannabis*, exhibiting varied effects.

In select embodiments of the present disclosure, the cannabinoid is a compound found in a mammal, sometimes called an endocannabinoid.

In select embodiments of the present disclosure, the cannabinoid is made in a laboratory setting, sometimes called a synthetic cannabinoid. In one embodiment, the cannabinoid is derived or obtained from a natural source (e.g. plant) but is subsequently modified or derivatized in one or more different ways in a laboratory setting, sometimes called a semi-synthetic cannabinoid.

In many cases, a cannabinoid can be identified because its chemical name will include the text string "*cannabi*". However, there are a number of cannabinoids that do not use this nomenclature, such as for example those described herein.

As well, any and all isomeric, enantiomeric, or optically active derivatives are also encompassed. In particular, where appropriate, reference to a particular cannabinoid includes both the "A Form" and the "B Form". For example, it is known that THCA has two isomers, THCA-A in which the carboxylic acid group is in the 1 position between the hydroxyl group and the carbon chain (A Form) and THCA-B in which the carboxylic acid group is in the 3 position following the carbon chain (B Form).

Examples of cannabinoids include, but are not limited to, Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Δ6-Cannabidiol (Δ6-CBD), Cannabidiol monomethylether (CBDM), Cannabidiol-C4 (CBD-C4), Cannabidivarinic Acid (CBDVA), Cannabidivarin (CBDV), Cannabidiorcol (CBD-C1), Tetrahydrocannabinolic acid A (THCA-A), Tetrahydrocannabinolic acid B (THCA-B), Tetrahydrocannabinol (THC or Δ9-THC), Δ8-tetrahydrocannabinol (Δ8-THC), trans-Δ10-tetrahydrocannabinol (trans-Δ10-THC), cis-Δ10-tetrahydrocannabinol (cis-Δ10-THC), Tetrahydrocannabinolic acid C4 (THCA-C4), Tetrahydrocannabinol C4 (THC-C4), Tetrahydrocannabivarinic acid (THCVA), Tetrahydrocannabivarin (THCV), Δ8-Tetrahydrocannabivarin (Δ8-THCV), Δ9-Tetrahydrocannabivarin (Δ9-THCV), Tetrahydrocannabiorcolic acid (THCA-C1), Tetrahydrocannabiorcol (THC-C1), Δ7-cis-iso-tetrahydrocannabivarin, Δ8-tetrahydrocannabinolic acid (Δ8-THCA), Δ9-tetrahydrocannabinolic acid (Δ9-THCA), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabinolic acid (CBNA), Cannabinol (CBN), Cannabinol methylether (CBNM), Cannabinol-C4 (CBN-C4), Cannabivarin (CBV), Cannabino-C2 (CBN-C2), Cannabiorcol (CBN-C1), Cannabinodiol (CBND), Cannabinodivarin (CBDV), Cannabitriol (CBT), 11-hydroxy-Δ9-tetrahydrocannabinol (11-ΔOH-THC), 11 nor 9-carboxy-Δ9-tetrahydrocannabinol, Ethoxy-cannabitriolvarin (CBTVE), 10-Ethoxy-9-hydroxy-Δ6a-tetrahydrocannabinol, Cannabitriolvarin (CBTV), 8,9 Dihydroxy-Δ6a(10a)-tetrahydrocannabinol (8,9-Di-OH-CBT-Δ5), Dehydrocannabifuran (DCBF), Cannbifuran (CBF), Cannabichromanon (CBCN), Cannabicitran, 10-Oxo-Δ6a(10a)-tetrahydrocannabinol (OTHC), Δ9-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E, 4E, 8Z, 10Z-tetraenoic acid isobutylamide, hexahydrocannibinol, and Dodeca-2E,4E-dienoic acid isobutylamide.

As used herein, the term "THC" refers to tetrahydrocannabinol. "THC" is used interchangeably herein with "Δ9-THC".

In select embodiments of the present disclosure, the THC-rich cannabinoid mixture may comprise THC (Δ9-THC), Δ8-THC, trans-Δ10-THC, cis-Δ10-THC, THCV, Δ8-THCV, Δ9-THCV, CBD, CBDA, CBDV, CBDVA, CBC, CBCA, CBCV, CBG, CBGV, CBN, CBNV, CBND, CBNDV, CBE, CBEV, CBL, CBLV, CBT, or cannabicitran Structural formulae of cannabinoids of the present disclosure may include the following:

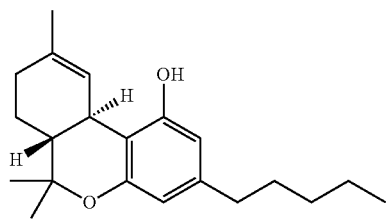

THC

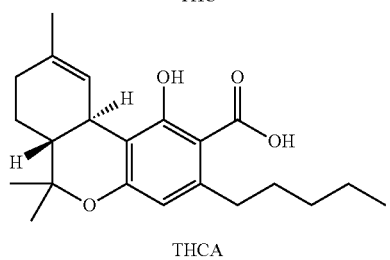

THCA

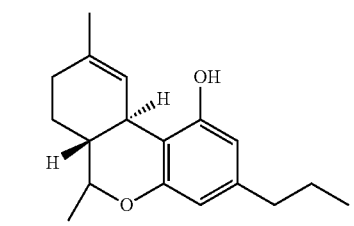

THCV

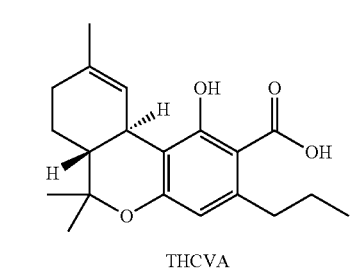

THCVA

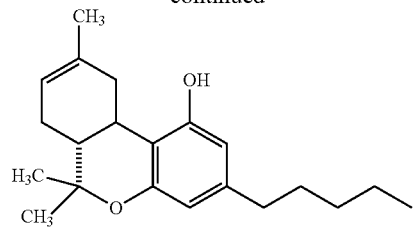

Δ8-THC

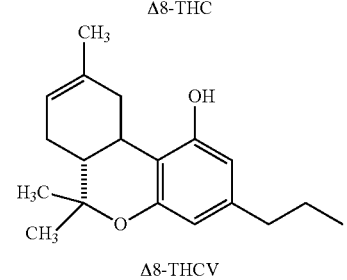

Δ8-THCV

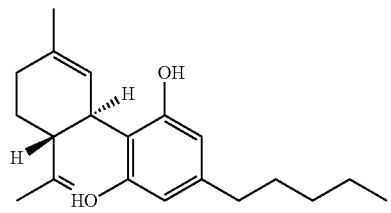

CBD

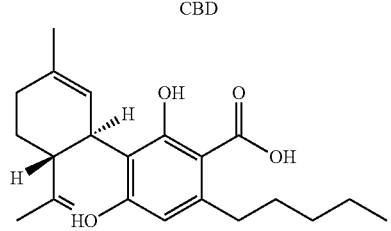

CBDA

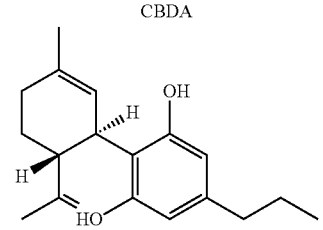

CBDV

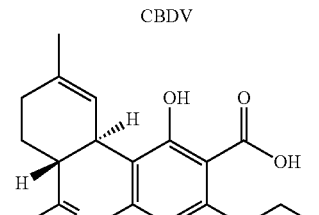

CBDVA

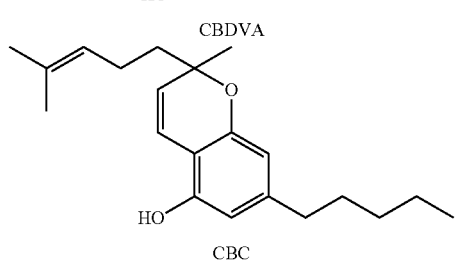

CBC

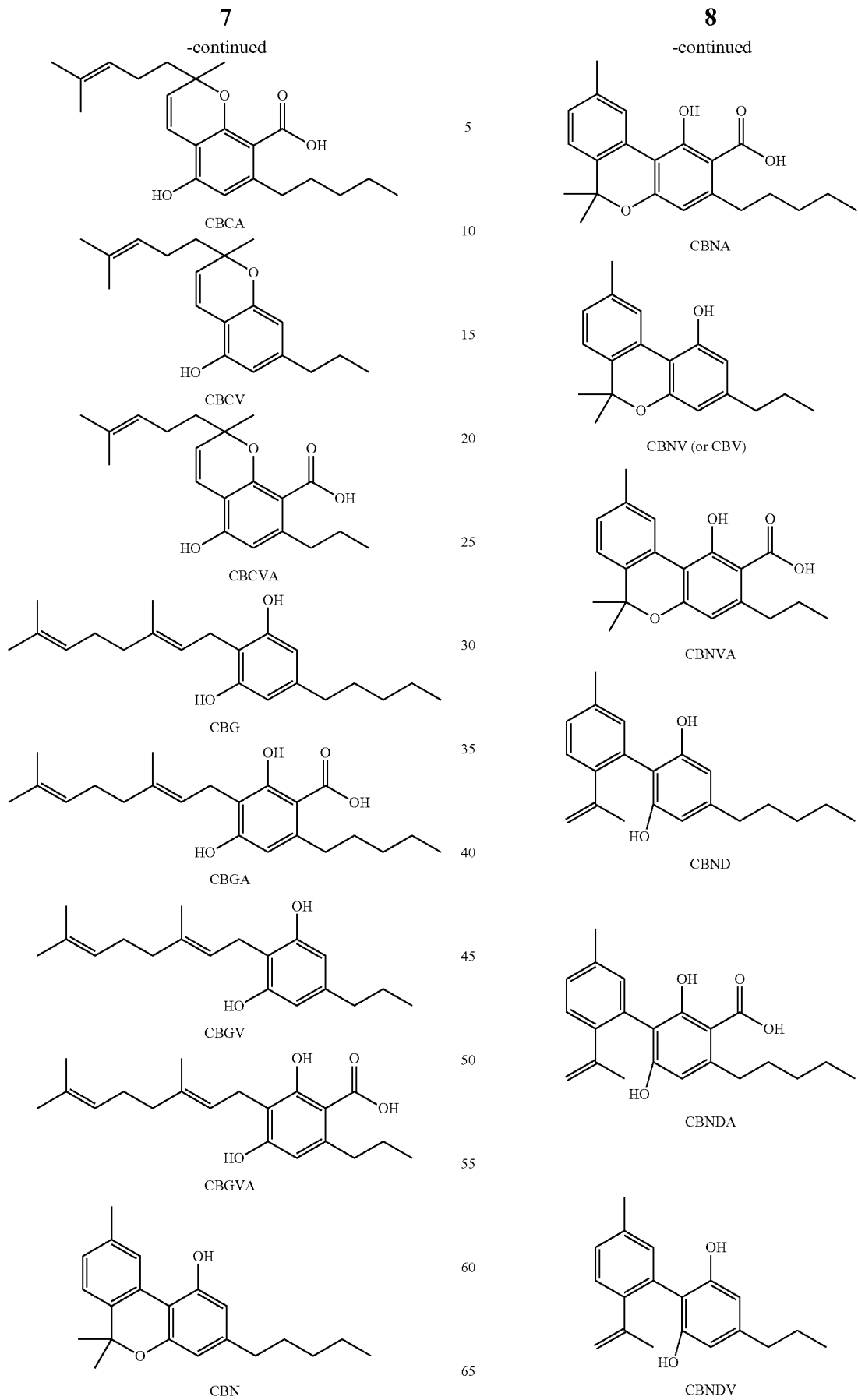

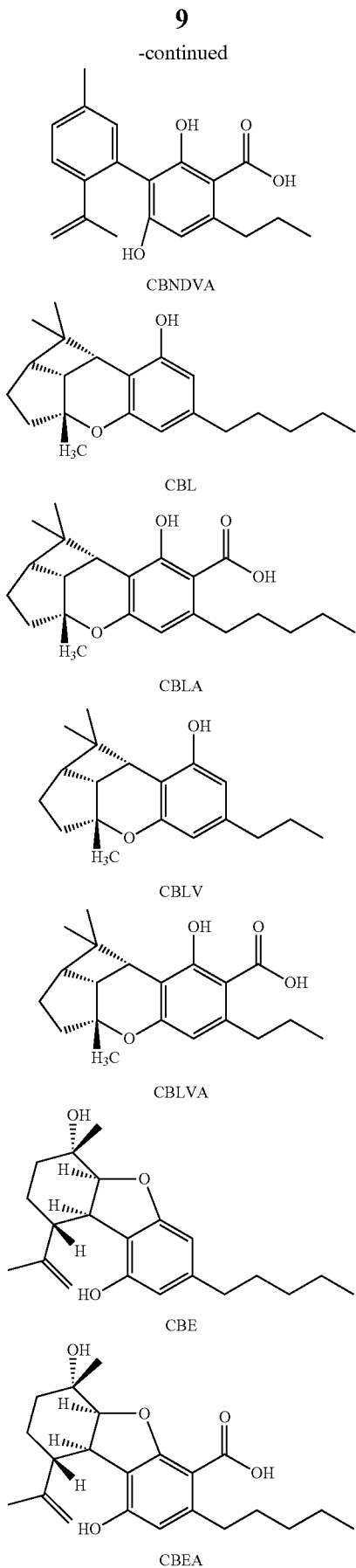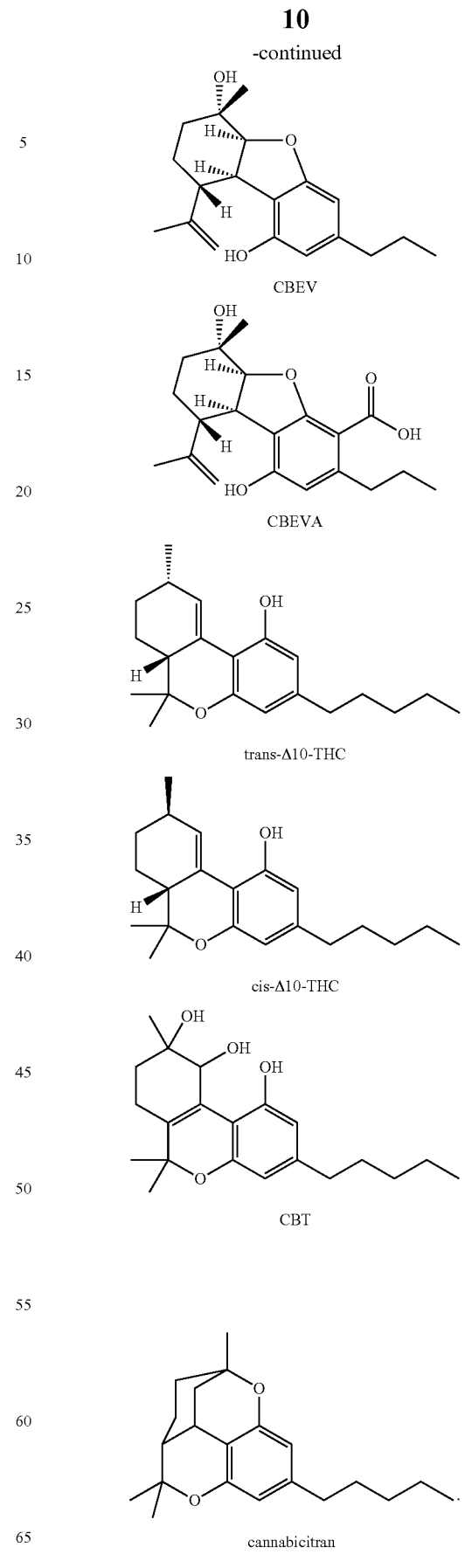

In select embodiments of the present disclosure, the benzoquinone reagent may comprise a compound as defined in formula (I) or formula (II):

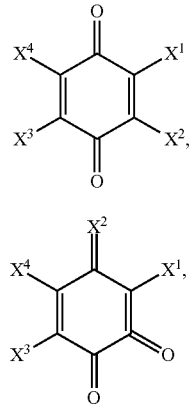

wherein $X^1$, $X^2$, $X^3$, and $X^4$ are each independently: H; a halide; a $C_{<12}$-hydrocarbyl; a $C_{<12}$-heteroaryl; a $C_{<12}$-heteroaralkyl; a $C_{<12}$-heteroaralkenyl; hydroxyl; a $C_{<12}$-alkoxy; a $C_{<12}$-amino; a $C_{<12}$-acyl; a $C_{<12}$-amide; a $C_{<12}$-ester; a $C_{<12}$-ketone; or a substituted analog thereof.

In select embodiments of the present disclosure, the benzoquinone reagent may comprise:

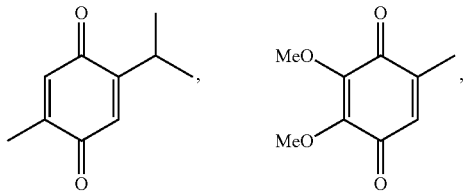

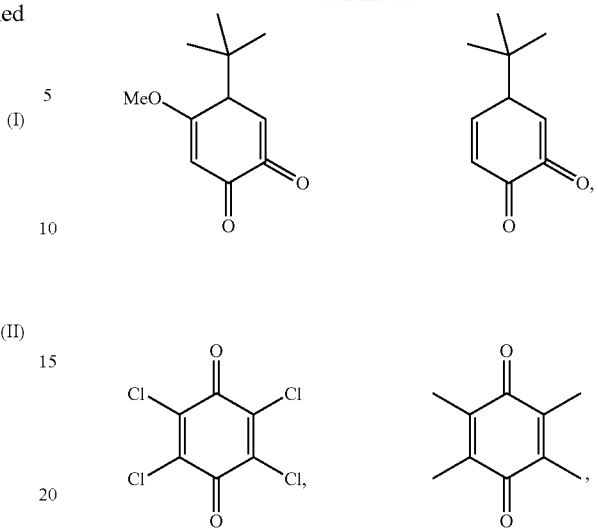

or a combination thereof.

In select embodiments of the present disclosure, the benzoquinone reagent may have an oxidation potential as set out in TABLE 1, which provides oxidation potentials for a series of benzoquinone reagents under non-limiting example conditions. Those skilled in the art who have benefited from the teachings of the present disclosure will readily understand the methods and standards required to determine the oxidation potential of any given benzoquinone reagent. Moreover, those skilled in the art who have benefited from the teaching of the present disclosure will recognize that the oxidation potential of any given benzoquinone reagent may be influenced by external factors such as solvent, pH, solute compositions, solute concentration, and the like.

TABLE 1

Oxidation potentials for a series of benzoquinone reagents under non-limiting example conditions.

| $X^1$ | $X^2$ | $X^3$ | $X^4$ | $\Sigma\sigma$ | $E°$ [Q/Q-] | $E°$ [Q-/Q$^{2-}$] | $E°$ [HQ/HQ-] | $E°$ [Q, H$^+$/HQ-] | $E°$ [Q, 2H$^+$/H$_2$Q] |
|---|---|---|---|---|---|---|---|---|---|
| H | H | H | H | 0.000 | 0.099 | 0.023 | 0.450 | 0.398 | 0.690 |
| C$_6$H$_5$ | H | H | H | −0.010 | 0.072 | 0.052 | 0.415 | 0.384 | 0.635 |
| CH$_3$ | H | H | H | −0.170 | 0.007 | −0.030 | 0.349 | 0.325 | 0.636 |
| C(CH$_3$)$_3$ | H | H | H | −0.200 | −0.041 | −0.096 | 0.320 | 0.294 | 0.602 |
| OCH$_3$ | H | H | H | −0.260 | −0.039 | −0.049 | 0.309 | 0.289 | 0.571 |
| N(CH$_3$)$_2$ | H | H | H | −0.830 | −0.221 | −0.144 | 0.124 | 0.182 | 0.466 |
| NH$_2$ | H | H | H | −0.660 | −0.193 | −0.117 | 0.042 | 0.175 | 0.456 |
| CH$_2$CH$_3$ | H | H | H | −0.150 | −0.025 | −0.068 | 0.321 | 0.300 | 0.605 |
| OH | H | H | H | −0.370 | 0.013 | −0.025 | 0.333 | 0.320 | 0.605 |
| OCH$_2$CH$_3$ | H | H | H | −0.280 | −0.070 | −0.069 | 0.300 | 0.271 | 0.541 |
| F | H | H | H | 0.340 | 0.231 | 0.153 | 0.559 | 0.467 | 0.687 |
| Cl | H | H | H | 0.370 | 0.242 | 0.195 | 0.595 | 0.491 | 0.706 |
| Br | H | H | H | 0.390 | 0.243 | 0.191 | 0.618 | 0.507 | 0.672 |
| SH | H | H | H | 0.150 | 0.110 | 0.086 | 0.436 | 0.403 | 0.665 |
| SiH$_3$ | H | H | H | 0.100 | 0.156 | 0.070 | 0.493 | 0.423 | 0.657 |
| CHO | H | H | H | 1.030 | 0.393 | 0.362 | 0.635 | 0.650 | 0.905 |
| COOCH$_3$ | H | H | H | 0.750 | 0.339 | 0.260 | 0.594 | 0.635 | 0.866 |
| CF$_3$ | H | H | H | 0.540 | 0.365 | 0.263 | 0.716 | 0.584 | 0.733 |
| CN | H | H | H | 1.000 | 0.479 | 0.401 | 0.853 | 0.686 | 0.778 |
| COOH | H | H | H | 0.770 | 0.592 | −0.068 | 0.621 | 0.644 | 0.799 |
| SO3— | H | H | H | 0.580 | 0.184 | 0.160 | 0.504 | 0.502 | 0.776 |
| NO2 | H | H | H | 1.270 | 0.613 | 0.688 | 1.007 | 0.833 | 0.938 |
| COCH$_3$ | H | H | H | 0.840 | 0.276 | 0.299 | 0.573 | 0.640 | 0.879 |
| C$_6$H$_5$ | C$_6$H$_5$ | H | H | −0.020 | 0.012 | 0.008 | 0.381 | 0.339 | 0.607 |

TABLE 1-continued

Oxidation potentials for a series of benzoquinone reagents under non-limiting example conditions.

| X$^1$ | X$^2$ | X$^3$ | X$^4$ | Σσ | E° [Q/Q−] | E° [Q−/Q$^{2-}$] | E° [HQ/HQ−] | E° [Q, H+/HQ−] | E° [Q, 2H+/H$_2$Q] |
|---|---|---|---|---|---|---|---|---|---|
| CH$_3$ | CH$_3$ | H | H | −0.340 | −0.090 | −0.133 | 0.297 | 0.262 | 0.564 |
| C(CH$_3$)$_3$ | C(CH$_3$)$_3$ | H | H | −0.400 | −0.385 | −0.249 | 0.099 | 0.047 | 0.355 |
| OCH$_3$ | OCH$_3$ | H | H | −0.520 | −0.048 | 0.065 | 0.404 | 0.333 | 0.563 |
| N(CH$_3$)$_2$ | N(CH$_3$)$_2$ | H | H | −1.660 | −0.301 | −0.117 | 0.236 | 0.119 | 0.398 |
| NH$_2$ | NH$_2$ | H | H | −1.320 | −0.172 | −0.144 | 0.101 | 0.152 | 0.384 |
| CH$_2$CH$_3$ | CH$_2$CH$_3$ | H | H | −0.300 | −0.113 | −0.118 | 0.257 | 0.238 | 0.549 |
| OH | OH | H | H | −0.740 | 0.041 | 0.028 | 0.370 | 0.339 | 0.527 |
| OCH$_2$CH$_3$ | OCH$_2$CH$_3$ | H | H | −0.560 | −0.086 | 0.137 | 0.373 | 0.340 | 0.581 |
| F | F | H | H | 0.680 | 0.374 | 0.282 | 0.706 | 0.526 | 0.671 |
| Cl | Cl | H | H | 0.740 | 0.342 | 0.320 | 0.726 | 0.524 | 0.663 |
| Br | Br | H | H | 0.780 | 0.330 | 0.315 | 0.699 | 0.536 | 0.681 |
| SH | SH | H | H | 0.300 | 0.112 | 0.851 | 0.271 | 0.349 | 0.571 |
| SiH$_3$ | SiH$_3$ | H | H | 0.200 | 0.191 | 0.237 | 0.589 | 0.450 | 0.645 |
| CHO | CHO | H | H | 2.060 | 0.658 | 0.835 | 1.064 | 0.942 | 0.974 |
| COOCH$_3$ | COOCH$_3$ | H | H | 1.500 | 0.445 | 0.417 | 0.732 | 0.707 | 0.866 |
| CF$_3$ | CF$_3$ | H | H | 0.540 | 0.365 | 0.263 | 0.716 | 0.584 | 0.733 |
| CN | CN | H | H | 2.000 | 0.886 | 0.856 | 1.210 | 0.914 | 0.912 |
| COOH | COOH | H | H | 1.540 | 0.770 | 0.125 | 0.819 | 0.766 | 0.817 |
| SO3— | SO3— | H | H | 1.160 | 0.184 | 0.265 | 0.535 | 0.600 | 0.798 |
| NO2 | NO2 | H | H | 2.540 | 0.983 | 1.378 | 1.460 | 1.115 | 1.007 |
| COCH$_3$ | COCH$_3$ | H | H | 1.680 | 0.421 | 0.433 | 0.833 | 0.689 | 0.788 |
| C$_6$H$_5$ | H | C$_6$H$_5$ | H | −0.020 | 0.041 | 0.104 | 0.404 | 0.351 | 0.634 |
| CH$_3$ | H | CH$_3$ | H | −0.340 | −0.092 | −0.081 | 0.348 | 0.285 | 0.574 |
| C(CH$_3$)$_3$ | H | C(CH$_3$)$_3$ | H | −0.400 | −0.193 | −0.193 | 0.201 | 0.185 | 0.520 |
| OCH$_3$ | H | OCH$_3$ | H | −0.520 | −0.146 | −0.233 | 0.120 | 0.133 | 0.459 |
| N(CH$_3$)$_2$ | H | N(CH$_3$)$_2$ | H | −1.660 | −0.602 | −0.284 | −0.043 | −0.072 | 0.288 |
| NH$_2$ | H | NH$_2$ | H | −1.320 | −0.614 | −0.360 | −0.233 | −0.178 | 0.116 |
| CH$_2$CH$_3$ | H | CH$_2$CH$_3$ | H | −0.300 | −0.172 | −0.168 | 0.214 | 0.188 | 0.514 |
| OH | H | OH | H | −0.740 | −0.142 | −0.108 | 0.237 | 0.196 | 0.485 |
| OCH$_2$CH$_3$ | H | OCH$_2$CH$_3$ | H | −0.560 | −0.285 | −0.190 | 0.099 | 0.090 | 0.385 |
| F | H | F | H | 0.680 | 0.344 | 0.270 | 0.691 | 0.509 | 0.667 |
| Cl | H | Cl | H | 0.740 | 0.372 | 0.356 | 0.751 | 0.547 | 0.718 |
| Br | H | Br | H | 0.780 | 0.377 | 0.352 | 0.744 | 0.569 | 0.730 |
| SH | H | SH | H | 0.300 | 0.100 | 0.136 | 0.486 | 0.368 | 0.615 |
| SiH$_3$ | H | SiH$_3$ | H | 0.200 | 0.194 | 0.151 | 0.545 | 0.445 | 0.675 |
| CHO | H | CHO | H | 2.060 | 0.628 | 0.569 | 0.953 | 0.858 | 1.083 |
| COOCH$_3$ | H | COOCH$_3$ | H | 1.500 | 0.490 | 0.398 | 0.841 | 0.786 | 1.058 |
| CF$_3$ | H | CF$_3$ | H | 1.080 | 0.614 | 0.487 | 0.959 | 0.712 | 0.803 |
| CN | H | CN | H | 2.000 | 0.814 | 0.720 | 1.149 | 0.852 | 0.876 |
| COOH | H | COOH | H | 1.540 | 0.997 | −0.252 | 0.901 | 0.812 | 0.924 |
| SO3— | H | SO3— | H | 1.160 | 0.307 | 0.270 | 0.637 | 0.599 | 0.889 |
| NO2 | H | NO2 | H | 2.540 | 0.981 | 0.975 | 1.362 | 1.081 | 1.128 |
| COCH$_3$ | H | COCH$_3$ | H | 1.680 | 0.463 | 0.363 | 0.718 | 0.739 | 1.076 |
| C$_6$H$_5$ | H | H | C$_6$H$_5$ | −0.020 | 0.019 | 0.070 | 0.364 | 0.345 | 0.599 |
| CH$_3$ | H | H | CH$_3$ | −0.340 | −0.088 | −0.095 | 0.241 | 0.258 | 0.553 |
| C(CH$_3$)$_3$ | H | H | C(CH$_3$)$_3$ | −0.400 | −0.192 | −0.274 | 0.124 | 0.157 | 0.467 |
| OCH$_3$ | H | H | OCH$_3$ | −0.520 | −0.154 | −0.123 | 0.148 | 0.215 | 0.493 |
| N(CH$_3$)$_2$ | H | H | N(CH$_3$)$_2$ | −1.660 | −0.468 | −0.255 | −0.017 | 0.037 | 0.338 |
| NH$_2$ | H | H | NH$_2$ | −1.320 | −0.345 | −0.265 | −0.143 | 0.020 | 0.285 |
| CH$_2$CH$_3$ | H | H | CH$_2$CH$_3$ | −0.300 | −0.142 | −0.143 | 0.199 | 0.204 | 0.506 |
| OH | H | H | OH | −0.740 | −0.034 | −0.060 | 0.263 | 0.269 | 0.518 |
| OCH$_2$CH$_3$ | H | H | OCH$_2$CH$_3$ | −0.560 | −0.173 | −0.167 | 0.164 | 0.175 | 0.438 |
| F | H | H | F | 0.680 | 0.382 | 0.286 | 0.679 | 0.551 | 0.675 |
| Cl | H | H | Cl | 0.740 | 0.389 | 0.350 | 0.745 | 0.584 | 0.683 |
| Br | H | H | Br | 0.780 | 0.387 | 0.358 | 0.776 | 0.616 | 0.734 |
| SH | H | H | SH | 0.300 | 0.135 | 0.149 | 0.439 | 0.402 | 0.548 |
| SiH$_3$ | H | H | SiH$_3$ | 0.200 | 0.203 | 0.148 | 0.569 | 0.474 | 0.615 |
| CHO | H | H | CHO | 2.060 | 0.634 | 0.673 | 0.990 | 0.880 | 1.021 |
| COOCH3 | H | H | COOCH3 | 1.500 | 0.518 | 0.437 | 0.775 | 0.740 | 0.939 |
| CF$_3$ | H | H | CF$_3$ | 1.080 | 0.620 | 0.496 | 1.025 | 0.785 | 0.797 |
| CN | H | H | CN | 2.000 | 0.815 | 0.734 | 1.285 | 0.970 | 0.874 |
| COOH | H | H | COOH | 1.540 | 0.988 | −0.106 | 0.809 | 0.788 | 0.847 |
| SO3— | H | H | SO3— | 1.160 | 0.302 | 0.269 | 0.614 | 0.574 | 0.810 |
| NO2 | H | H | NO2 | 2.540 | 0.944 | 1.081 | 1.488 | 1.102 | 1.047 |
| COCH$_3$ | H | H | COCH$_3$ | 1.680 | 0.375 | 0.513 | 0.740 | 0.720 | 0.926 |
| C$_6$H$_5$ | C$_6$H$_5$ | C$_6$H$_5$ | H | −0.030 | −0.024 | 0.014 | 0.334 | 0.324 | 0.588 |
| CH$_3$ | CH$_3$ | CH$_3$ | H | −0.510 | −0.211 | −0.192 | 0.162 | 0.158 | 0.485 |
| C(CH$_3$)$_3$ | C(CH$_3$)$_3$ | C(CH$_3$)$_3$ | H | −0.600 | −0.560 | −0.468 | −0.088 | −0.079 | 0.229 |
| OCH$_3$ | OCH$_3$ | OCH$_3$ | H | −0.780 | −0.213 | −0.010 | 0.233 | 0.213 | 0.455 |
| N(CH$_3$)$_2$ | N(CH$_3$)$_2$ | N(CH$_3$)$_2$ | H | −2.490 | −0.699 | −0.262 | −0.136 | −0.027 | 0.370 |
| NH$_2$ | NH$_2$ | NH$_2$ | H | −1.980 | −0.556 | −0.361 | −0.163 | −0.129 | 0.120 |
| CH$_2$CH$_3$ | CH$_2$CH$_3$ | CH$_2$CH$_3$ | H | −0.450 | −0.223 | −0.205 | 0.125 | 0.154 | 0.491 |
| OH | OH | OH | H | −1.110 | −0.079 | −0.030 | 0.246 | 0.235 | 0.444 |
| OCH$_2$CH$_3$ | OCH$_2$CH$_3$ | OCH$_2$CH$_3$ | H | −0.840 | −0.290 | 0.048 | 0.236 | 0.205 | 0.465 |
| F | F | F | H | 1.110 | 0.499 | 0.405 | 0.824 | 0.606 | 0.691 |

TABLE 1-continued

Oxidation potentials for a series of benzoquinone reagents under non-limiting example conditions.

| $X^1$ | $X^2$ | $X^3$ | $X^4$ | $\Sigma\sigma$ | $E°$ [Q/Q-] | $E°$ [Q-/Q$^2$-] | $E°$ [HQ/HQ-] | $E°$ [Q, H$^+$/HQ-] | $E°$ [Q, 2H$^+$/H$_2$Q] |
|---|---|---|---|---|---|---|---|---|---|
| Cl | Cl | Cl | H | 1.170 | 0.472 | 0.472 | 0.877 | 0.626 | 0.698 |
| Br | Br | Br | H | 0.450 | 0.462 | 0.477 | 0.848 | 0.643 | 0.720 |
| SH | SH | SH | H | 0.450 | 0.117 | 0.217 | 0.511 | 0.407 | 0.491 |
| SiH$_3$ | SiH$_3$ | SiH$_3$ | H | 0.300 | 0.233 | 0.272 | 0.611 | 0.475 | 0.611 |
| CHO | CHO | CHO | H | 3.090 | 0.796 | 0.978 | 1.257 | 1.072 | 1.167 |
| COOCH3 | COOCH3 | COOCH3 | H | 2.250 | 0.586 | 0.559 | 0.938 | 0.849 | 1.053 |
| CF$_3$ | CF$_3$ | CF$_3$ | H | 1.620 | 0.845 | 0.748 | 1.292 | 0.918 | 0.875 |
| CN | CN | CN | H | 3.000 | 1.178 | 1.122 | 1.553 | 1.134 | 0.968 |
| COOH | COOH | COOH | H | 2.310 | 1.149 | −0.065 | 1.060 | 0.929 | 0.966 |
| SO3— | SO3— | SO3— | H | 1.740 | 0.256 | 0.353 | 0.646 | 0.665 | 0.902 |
| NO2 | NO2 | NO2 | H | 3.810 | 1.261 | 1.510 | 1.701 | 1.269 | 1.147 |
| COCH$_3$ | COCH$_3$ | COCH$_3$ | H | 2.520 | 0.557 | 0.518 | 0.935 | 0.865 | 0.898 |
| C$_6$H$_5$ | C$_6$H$_5$ | C$_6$H$_5$ | C$_6$H$_5$ | −0.040 | −0.084 | 0.009 | 0.367 | 0.281 | 0.561 |
| CH$_3$ | CH$_3$ | CH$_3$ | CH$_3$ | −0.040 | −0.084 | 0.009 | 0.367 | 0.281 | 0.561 |
| C(CH$_3$)$_3$ | C(CH$_3$)$_3$ | C(CH$_3$)$_3$ | C(CH$_3$)$_3$ | −0.800 | −1.107 | −0.804 | −0.388 | −0.509 | −0.153 |
| OCH$_3$ | OCH$_3$ | OCH$_3$ | OCH$_3$ | −1.040 | −0.229 | 0.111 | 0.370 | 0.220 | 0.465 |
| N(CH$_3$)$_2$ | N(CH$_3$)$_2$ | N(CH$_3$)$_2$ | N(CH$_3$)$_2$ | −3.320 | −0.629 | −0.322 | −0.253 | −0.138 | 0.203 |
| NH$_2$ | NH$_2$ | NH$_2$ | NH$_2$ | −2.640 | −0.571 | −0.456 | −0.197 | −0.192 | 0.028 |
| CH$_2$CH$_3$ | CH$_2$CH$_3$ | CH$_2$CH$_3$ | CH$_2$CH$_3$ | −0.600 | −0.372 | −0.347 | 0.066 | 0.032 | 0.384 |
| OH | OH | OH | OH | −1.480 | −0.077 | −0.039 | 0.295 | 0.183 | 0.379 |
| OCH$_2$CH$_3$ | OCH$_2$CH$_3$ | OCH$_2$CH$_3$ | OCH$_2$CH$_3$ | −1.120 | −0.305 | 0.238 | 0.388 | 0.290 | 0.527 |
| F | F | F | F | 1.360 | 0.638 | 0.531 | 0.986 | 0.670 | 0.731 |
| Cl | Cl | Cl | Cl | 1.480 | 0.564 | 0.588 | 1.003 | 0.663 | 0.684 |
| Br | Br | Br | Br | 1.560 | 0.539 | 0.581 | 0.960 | 0.660 | 0.720 |
| SH | SH | SH | SH | 0.600 | 0.111 | 0.279 | 0.526 | 0.342 | 0.453 |
| SiH$_3$ | SiH$_3$ | SiH$_3$ | SiH$_3$ | 0.400 | 0.247 | 0.322 | 0.675 | 0.459 | 0.558 |
| CHO | CHO | CHO | CHO | 4.120 | 0.873 | 1.005 | 1.319 | 1.099 | 1.221 |
| COOCH$_3$ | COOCH$_3$ | COOCH$_3$ | COOCH$_3$ | 3.000 | 0.744 | 0.680 | 1.064 | 0.909 | 1.052 |
| CF$_3$ | CF$_3$ | CF$_3$ | CF$_3$ | 2.160 | 0.972 | 0.902 | 1.397 | 0.937 | 0.833 |
| CN | CN | CN | CN | 4.000 | 1.48 | 1.430 | 1.832 | 1.271 | 1.025 |
| COOH | COOH | COOH | COOH | 3.080 | 1.278 | 0.068 | 1.143 | 0.970 | 0.980 |
| SO3— | SO3— | SO3— | SO3— | 2.320 | 0.084 | 0.348 | 0.613 | 0.546 | 0.846 |
| NO$_2$ | NO$_2$ | NO$_2$ | NO$_2$ | 5.080 | 1.613 | 1.662 | 1.939 | 1.441 | 1.231 |
| COCH$_3$ | COCH$_3$ | COCH$_3$ | COCH$_3$ | 3.360 | 0.663 | 0.657 | 0.914 | 0.768 | 0.865 |
| CN | CN | Cl | Cl | 2.740 | 1.096 | 1.079 | 1.461 | 1.027 | 0.884 |

See: Huynh et al., "Quinone 1 e- and 2 e-/2 H$^+$ Reduction Potentials: Identification and Analysis of Deviations from Systematic Scaling Relationships", J. Am. Chem. Soc. 2016, 138(49): S1-S34.

In select embodiments of the present disclosure, the contacting of the THC-rich cannabinoid mixture with the benzoquinone reagent may comprise introducing the benzoquinone reagent to the THC-rich cannabinoid mixture at a benzoquinone:THC ratio of between: (i) about 1.0:1.0 and about 10.0:1.0 on a molar basis; or (ii) about 2.0:1.0 and about 7.0:1.0 on a molar basis. In a particular embodiment, the benzoquinone:THC ratio is about 2.5:1.0, about 2.6:1.0, about 2.7:1.0, about 2.8:1.0, about 2.9:1.0, about 3.0:1.0, about 3.1:1.0, about 3.2:1.0, about 3.3:1.0, about 3.4:1.0, or about 3.5:1.0 on a molar basis.

In the context of the present disclosure, the relative quantities of cannabinoids may be expressed as a ratio such as THC:CBN or THC:CBD. Those skilled in the art will recognize that a variety of analytical methods may be used to determine such ratios, and the protocols required to implement any such method are within the purview of those skilled in the art. By way of non-limiting example, such ratios may be determined by diode-array-detector high pressure liquid chromatography, UV-detector high pressure liquid chromatography, nuclear magnetic resonance spectroscopy, mass spectroscopy, flame-ionization gas chromatography, gas chromatograph-mass spectroscopy, or combinations thereof.

In select embodiments of the present disclosure, the target reaction-temperature range may be between: (i) about 20° C. and about 190° C.; or (ii) about 60° C. and about 130° C. In a particular embodiment, the target reaction temperature is about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., about 110° C., about 111° C., about 112° C., about 113° C., about 114° C., or about 115° C. Those skilled in the art who have benefitted from the teachings of the present disclosure will recognize that selecting a target-reaction temperature range may be done having regard to the particulars of the input material, the desired extent of upgrading, the particulars of the benzoquinone reagent, the particulars of the solvent system (or lack thereof), the reaction time, and the like.

In select embodiments of the present disclosure, the target reaction-time range may be between: (i) about 1 h and about 100 h; or (ii) about 20 h and about 80 h. In a particular embodiment, the reaction time is about 2 h, about 4 h, about 6 h, about 8 h, or about 10 h. In another particular embodiment, the reaction time is about about 16 h, about 20 h, about 24 h, about 30 h, or about 36 h. In a further particular embodiment, the reaction time is about 40 h, about 44 h, about 48 h, about 52 h, or about 56 h. Those skilled in the art who have benefitted from the teachings of the present disclosure will recognize that selecting a target-reaction time range may be done having regard to the particulars of the input material, the desired extent of upgrading, the particulars of the benzoquinone reagent, the particulars of the solvent system (or lack thereof), the reaction temperature, and the like.

In select embodiments of the present disclosure, the contacting of the cannabinoid mixture with the benzoquinone reagent may be executed in the presence of a solvent. The solvent may be pentane, hexane, heptane, methanol, ethanol, isopropanol, dimethyl sulfoxide, acetone, ethyl acetate, diethyl ether, tert-butyl methyl ether, water, acetic acid, anisole, 1-butanol, 2-butanol, butane, butyl acetate, ethyl formate, formic acid, isobutyl acetate, isopropyl acetate, methyl acetate, 3-methyl-1-butanol, methylethyl ketone, 2-methyl-1-propanol, 1-pentanol, 1-propanol, propane, propyl acetate, trimethylamine, or a combination thereof.

Select embodiments of the present disclosure relate to a method of converting a THC-rich cannabinoid mixture that comprises at least about 75% THC into a CBN-rich cannabinoid mixture that comprises at least about 40% CBN, the method comprising contacting the cannabinoid mixture with tetrachloro-1,4-benzoquinone under reaction conditions comprising: (i) a reaction temperature that is within a target reaction-temperature range; and (ii) a reaction time that is within a target reaction-time range.

Select embodiments of the present disclosure relate to a method of converting a THC-rich cannabinoid mixture that comprises at least about 75% THC into a CBN-rich cannabinoid mixture that comprises at least about 15% CBN, the method comprising contacting the cannabinoid mixture with 2-isopropyl-5-methyl-1,4-benzoquinone under reaction conditions comprising: (i) a reaction temperature that is within a target reaction-temperature range; and (ii) a reaction time that is within a target reaction-time range.

In select embodiments, the methods of converting a THC-rich cannabinoid mixture into a CBN-rich cannabinoid mixture may further comprise purifying the CBN-rich cannabinoid mixture. In an embodiment, the purification comprises chromatography, distillation, and/or crystallization. In an embodiment, the chromatography is normal phase flash chromatography and the distillation is short path distillation. In an embodiment, the crystallization may provide crystals suitable for single crystal X-ray diffraction.

In the context of the present disclosure, a converting a THC-rich cannabinoid mixture into a CBN-rich cannabinoid mixture requires a quantifiable decrease in THC content on a weigh-to-weight basis from the THC-rich cannabinoid mixture to the CBN rich-cannabinoid mixture. Likewise, converting a THC-rich cannabinoid mixture into a CBN-rich cannabinoid mixture requires a quantifiable increase in CBN content on a weigh-to-weight basis from the THC-rich cannabinoid mixture to the CBN rich-cannabinoid mixture. Those skilled in the at who have benefited from the teachings of the present disclosure will appreciate that converting a THC-rich cannabinoid mixture into a CBN rich cannabinoid mixture does not require that THC be the primary component of the THC-rich cannabinoid mixture, and does not require that CBN be the primary component of the CBN-rich cannabinoid.

In the context of the present disclosure, converting a THC-rich cannabinoid mixture into a CBN-rich cannabinoid mixture may equate to oxidizing THC to CBN. Accordingly, increases in the CBN content of a mixture of cannabinoids result from the methods of the present disclosure.

EXAMPLES

The following examples describe a series of experiments in which complex cannabinoid mixtures having a low THC content were contacted with various benzoquinone reagents to reduce the THC content of the complex cannabinoid mixtures according to non-limiting SCHEME 1.

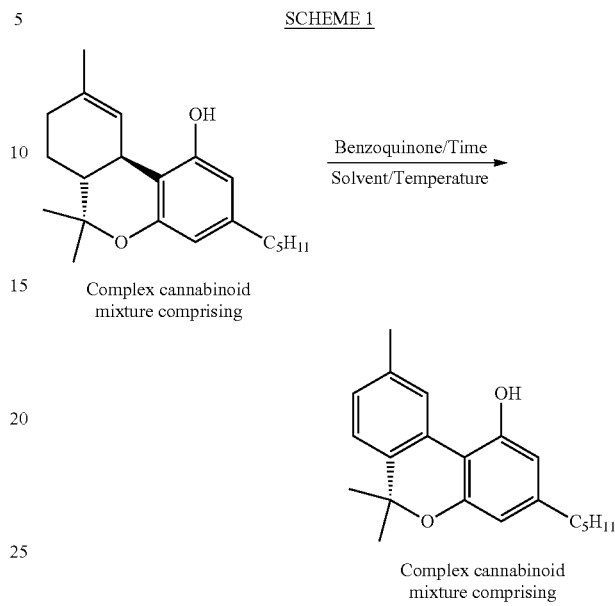

SCHEME 1

Complex cannabinoid mixture comprising

Complex cannabinoid mixture comprising

The complex cannabinoid mixture was a THC-rich marijuana distillate. Analysis by HPLC-DAD indicated that, in advance of the introduction of the benzoquinone reagent, the complex cannabinoid mixture comprised: (i) about 79.3 wt. % THC; (ii) about 9.8 wt. % CBD; and (iii) about 1.8 wt. % CBN.

Example 1

A mixture of the THC-rich marijuana distillate input material (2.02 g), heptane, and tetrachloro-1,4-benzoquinone (3.76 g, 15.28 mmol, about 3 equivalents relative to the THC content of the THC-rich marijuana distillate input material) was stirred and heated to 110° C. for 6 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 1.87 g of product material. The product material was analyzed by HPLC-DAD to obtain the results set out in TABLE 2.

TABLE 2

Experimental results from the THC-CBN conversion reaction of EXAMPLE 1.

| | Quantity (g) | THC (% w/w) | CBD (% w/w) | CBN (% w/w) | CBN Yield (%) | CBD Recovery (%) |
|---|---|---|---|---|---|---|
| Input Material | 2.02 | 79.3 | 9.8 | 1.8 | N/A | N/A |
| Product Material | 1.87 | 0.3 | 6.3 | 34.8 | 40.2 | 59.5 |

Example 2

A mixture of the THC-rich marijuana distillate input material (2.01 g), heptane (20 mL), and tetrachloro-1,4-benzoquinone (3.74 g, 15.21 mmol, about 3 equivalents relative to the THC content of the THC-rich marijuana distillate input material) was stirred and heated to 110° C. for 24 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 2.00 g of product material. The product material was analyzed by HPLC-DAD to obtain the results set out in TABLE 3.

TABLE 3

Experimental results from the THC-CBN conversion reaction of EXAMPLE 2.

|  | Quantity (g) | THC (% w/w) | CBD (% w/w) | CBN (% w/w) | CBN Yield (%) | CBD Recovery (%) |
|---|---|---|---|---|---|---|
| Input Material | 2.01 | 79.3 | 9.8 | 1.8 | N/A | N/A |
| Product Material | 2.00 | 0.2 | 2.6 | 29.3 | 36.4 | 26.4 |

Example 3

A mixture of the THC-rich marijuana distillate input material (0.77 g), ethyl acetate (10 mL), and tetrachloro-1,4-benzoquinone (1.43 g, 5.83 mmol, about 3 equivalents relative to the THC content of the THC-rich marijuana distillate input material) was stirred and heated to 85° C. for 24 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 0.74 g of product material. The product material was analyzed by HPLC-DAD to obtain the results set out in TABLE 4.

TABLE 4

Experimental results from the THC-CBN conversion reaction of EXAMPLE 3.

|  | Quantity (g) | THC (% w/w) | CBD (% w/w) | CBN (% w/w) | CBN Yield (%) | CBD Recovery (%) |
|---|---|---|---|---|---|---|
| Input Material | 0.77 | 79.3 | 9.8 | 1.8 | N/A | N/A |
| Product Material | 0.74 | 4.1 | 5.5 | 38.6 | 46.3 | 53.9 |

Example 4

A mixture of the THC-rich marijuana distillate input material (0.88 g), ethyl acetate (10 mL), and tetrachloro-1,4-benzoquinone (1.63 g, 6.64 mmol, about 3 equivalents relative to the THC content of the THC-rich marijuana distillate input material) was stirred and heated to 85° C. for 6 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 0.99 g of product material. The product material was analyzed by HPLC-DAD to obtain the results set out in TABLE 5.

TABLE 5

Experimental results from the THC-CBN conversion reaction of EXAMPLE 4.

|  | Quantity (g) | THC (% w/w) | CBD (% w/w) | CBN (% w/w) | CBN Yield (%) | CBD Recovery (%) |
|---|---|---|---|---|---|---|
| Input Material | 0.88 | 79.3 | 9.8 | 1.8 | N/A | N/A |
| Product Material | 0.99 | 9.8 | 6.8 | 46.8 | 65.8 | 78.2 |

Example 5

A mixture of the THC-rich marijuana distillate input material (0.99 g), ethyl acetate (10 mL), and tetrachloro-1,4-benzoquinone (1.86 g, 7.55 mmol, about 3 equivalents relative to the THC content of the THC-rich marijuana distillate input material) was stirred and heated to 85° C. for 24 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 1.12 g of product material. The product material was analyzed by HPLC-DAD to obtain the results set out in TABLE 6.

TABLE 6

Experimental results from the THC-CBN conversion reaction of EXAMPLE 5.

|  | Quantity (g) | THC (% w/w) | CBD (% w/w) | CBN (% w/w) | CBN Yield (%) | CBD Recovery (%) |
|---|---|---|---|---|---|---|
| Input Material | 0.99 | 79.3 | 9.8 | 1.8 | N/A | N/A |
| Product Material | 1.12 | 2.2 | 3.6 | 58.8 | 82.1 | 41.1 |

Example 6

A mixture of the THC-rich marijuana distillate input material (0.66 g), ethyl acetate (10 mL), and tetrachloro-1,4-benzoquinone (1.43 g, 5.80 mmol, about 3.5 equivalents relative to the THC content of the THC-rich marijuana distillate input material) was stirred and heated to 85° C. for 48 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 0.68 g of product material. The product material was analyzed by HPLC-DAD to obtain the results set out in TABLE 7.

TABLE 7

Experimental results from the THC-CBN conversion reaction of EXAMPLE 6.

| | Quantity (g) | THC (% w/w) | CBD (% w/w) | CBN (% w/w) | CBN Yield (%) | CBD Recovery (%) |
|---|---|---|---|---|---|---|
| Input Material | 0.66 | 79.3 | 9.8 | 1.8 | N/A | N/A |
| Product Material | 0.68 | 1.5 | 4.1 | 58.1 | 75.2 | 43.4 |

Example 7

A mixture of the THC-rich marijuana distillate input material (0.47 g), heptane (10 mL), and 2-isopropyl-5-methyl-1,4-benzoquinone (thymoquinone) (0.59 g, 3.59 mmol, about 3 equivalents relative to the THC content of the THC-rich marijuana distillate input material) was stirred and heated to 110° C. for 6 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 1.13 g of product material. The product material was analyzed by HPLC-DAD to obtain the results set out in TABLE 8.

TABLE 8

Experimental results from the THC-CBN conversion reaction of EXAMPLE 7.

| | Quantity (g) | THC (% w/w) | CBD (% w/w) | CBN (% w/w) | CBN Yield (%) | CBD Recovery (%) |
|---|---|---|---|---|---|---|
| Input Material | 0.47 | 79.3 | 9.8 | 1.8 | N/A | N/A |
| Product Material | 1.13 | 2.6 | 3.8 | 5.9 | 17.6 | 92.6 |

Example 8

A mixture of the THC-rich marijuana distillate input material (0.50 g), heptane (10 mL), and tetrachloro-1,4-benzoquinone (3.76 g, 15.28 mmol, about 3 equivalents relative to the THC content of the THC-rich marijuana distillate input material) was stirred and heated to 110° C. for 24 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 1.05 g of product material. The product material was analyzed by HPLC-DAD to obtain the results set out in TABLE 9.

TABLE 9

Experimental results from the THC-CBN conversion reaction of EXAMPLE 8.

| | Quantity (g) | THC (% w/w) | CBD (% w/w) | CBN (% w/w) | CBN Yield (%) | CBD Recovery (%) |
|---|---|---|---|---|---|---|
| Input Material | 0.50 | 79.3 | 9.8 | 1.8 | N/A | N/A |
| Product Material | 1.05 | 0.4 | 4.7 | 19.7 | 51.8 | 100.9 |

Example 9

A mixture of the THC-rich marijuana distillate input material (0.80 g), ethyl acetate (10 mL), and 2-isopropyl-5-methyl-1,4-benzoquinone (thymoquinone) (1.00 g, 6.06 mmol, about 3 equivalents relative to the THC content of the THC-rich marijuana distillate input material) was stirred and heated to 84° C. for 24 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 1.81 g of product material. The product material was analyzed by HPLC-DAD.

Example 10

A mixture of the THC-rich marijuana distillate input material (0.50 g), heptane (10 mL), and 4-tert-butyl-5-methoxy-1,2-benzoquinone (0.74 g, 3.78 mmol, about 3 equivalents relative to the THC content of the THC-rich marijuana distillate input material) was stirred and heated to 110° C. for 24 hours to form a crude product mixture. The crude product mixture was cooled to ambient temperature and concentrated in vacuo to provide a crude residue. The crude residue was triturated with heptane (20 mL) and loaded onto a silica gel plug (Davisil® silica gel, grade 633, 60A pore size, 200-425 mesh particle size, 10 g). The desired product was eluted under house vacuum with 100 mL of tert-butyl methyl ether and heptane (TBME/heptane (5/95 v/v)) and volatiles were concentrated in vacuo to 0.89 g of product material. The product material was analyzed by HPLC-DAD to obtain the results set out in TABLE 10.

TABLE 10

Experimental results from the THC-CBN conversion reaction of EXAMPLE 10.

| | Quantity (g) | THC (% w/w) | CBD (% w/w) | CBN (% w/w) | CBN Yield (%) | CBD Recovery (%) |
|---|---|---|---|---|---|---|
| Input Material | 0.50 | 79.3 | 9.8 | 1.8 | N/A | N/A |
| Product Material | 0.89 | 0.9 | 4.7 | 24.0 | 53.3 | 85.4 |

Example 11

A mixture of the THC-rich marijuana distillate input material (0.59 g), heptane (10 mL), and 2,3-dimethoxy-5-methyl-1,4-benzoquinone (Coenzyme $Q_0$) (0.81 g, 4.4 g mmol, about 3 equivalents relative to the THC content of the THC-rich marijuana distillate input material) was stirred and heated to 110° C. for 24 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 0.35 g of product material. The product material was analyzed by HPLC-DAD to obtain the results set out in TABLE 11.

TABLE 11

Experimental results from the THC-CBN conversion reaction of EXAMPLE 11.

|  | Quantity (g) | THC (% w/w) | CBD (% w/w) | CBN (% w/w) | CBN Yield (%) | CBD Recovery (%) |
|---|---|---|---|---|---|---|
| Input Material | 0.59 | 79.3 | 9.8 | 1.8 | N/A | N/A |
| Product Material | 0.35 | 3.4 | 6.1 | 18.7 | 13.9 | 37.1 |

Example 12

A mixture of the THC-rich marijuana distillate input material (0.58 g), heptane (10 mL), and tetramethyl-1,4-benzoquinone (0.72 g, 4.40 mmol, about 3 equivalents relative to the THC content of the THC-rich marijuana distillate input material) was stirred and heated to 110° C. for 6 hours to form a crude product mixture. The crude product mixture was cooled to ambient temperature and filtered using a Buchner funnel equipped with a glass frit to separate suspended solids from a filtrate. The filtrate was concentrated in vacuo to provide a crude product residue that was triturated with heptane (20 mL), filtered a second time using a Buchner funnel equipped with a glass frit, and concentrated in vacuo to provide 0.93 g of product material. The product material was analyzed by HPLC-DAD to obtain the results set out in TABLE 12.

TABLE 12

Experimental results from the THC-CBN conversion reaction of EXAMPLE 12.

|  | Quantity (g) | THC (% w/w) | CBD (% w/w) | CBN (% w/w) | CBN Yield (%) | CBD Recovery (%) |
|---|---|---|---|---|---|---|
| Input Material | 0.58 | 79.3 | 9.8 | 1.8 | N/A | N/A |
| Product Material | 0.932 | 33.6 | 4.5 | 1.4 | 2.8 | 73.5 |

Example 13

A CBN-rich cannabinoid mixture (about 58% CBN purity) was obtained as a resin by the methods of the present disclosure. The resin was purified by normal phase flash chromatography (TBME:heptane) to obtain a resin of about 85% CBN purity, which was further purified by short path distillation to obtain a resin with about 93% CBN purity. Crystallization of the 93% CBN resin from TBME yielded CBN crystals.

In the present disclosure, all terms referred to in singular form are meant to encompass plural forms of the same. Likewise, all terms referred to in plural form are meant to encompass singular forms of the same. Unless defined otherwise, all technical and scientific terms used herein have the same meaning as commonly understood by one of ordinary skill in the art to which this disclosure pertains.

As used herein, the term "about" refers to an approximately +/−10% variation from a given value. It is to be understood that such a variation is always included in any given value provided herein, whether or not it is specifically referred to.

It should be understood that the compositions and methods are described in terms of "comprising," "containing," or "including" various components or steps, the compositions and methods can also "consist essentially of or "consist of the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Although individual embodiments are discussed, the disclosure covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

Many obvious variations of the embodiments set out herein will suggest themselves to those skilled in the art in light of the present disclosure. Such obvious variations are within the full intended scope of the appended claims.

We claim:

1. A method of converting a tetrahydrocannabinol (THC)-rich cannabinoid mixture that comprises at least 20 wt. % THC into a cannabinol (CBN)-rich cannabinoid mixture that comprises at least 2.0 wt. % CBN, the method comprising reacting the cannabinoid mixture with a benzoquinone reagent, wherein the benzoquinone reagent comprises a compound as defined in formula (II):

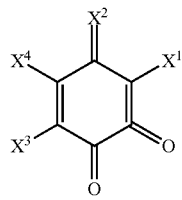

(II)

wherein $X^1$, $X^2$, $X^3$, and $X^4$ are each independently: H; a halide; a $C_{1-12}$-hydrocarbyl; a $C_{3-12}$-heteroaryl; a $C_{3-12}$-heteroaralkyl; a $C_{3-12}$-heteroaralkenyl; hydroxyl; a $C_{1-12}$-alkoxy; a $C_{0-12}$-amino; a $C_{1-12}$-acyl; a $C_{1-12}$-amide, a $C_{2-12}$-ester; or a $C_{2-12}$-ketone.

2. The method of claim 1, wherein the THC-rich cannabinoid mixture comprises at least about 80 wt. % THC.

3. The method of claim 1, wherein the THC-rich cannabinoid mixture comprises at least about 95 wt. % THC.

4. The method of claim 1, wherein the THC-rich cannabinoid mixture is derived from a marijuana biomass.

5. The method of claim 1, wherein the THC-rich cannabinoid mixture is a *cannabis* distillate, a *cannabis* resin, a *cannabis* extract, or a combination thereof.

6. The method of claim 1, wherein the benzoquinone reagent comprises:

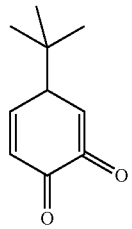 or 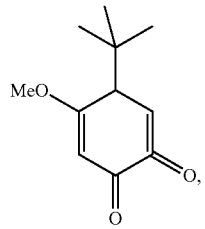

or a combination thereof.

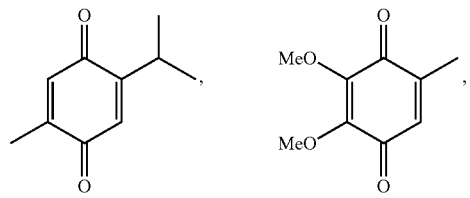

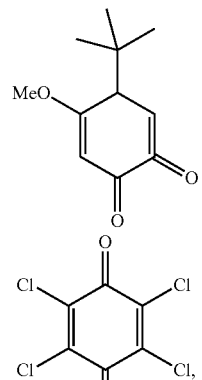

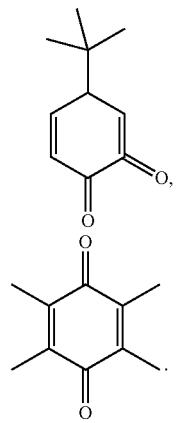

7. The method of claim 1, wherein the reacting of the THC-rich cannabinoid mixture with the benzoquinone reagent is at a benzoquinone:THC ratio of between 1.0:1.0 and 10.0:1.0 on a molar basis.

8. The method of claim 1, wherein the reacting of the THC-rich cannabinoid mixture with the benzoquinone reagent is at a benzoquinone:THC ratio of between 2.0:1.0 and 4.0:1.0 on a molar basis.

9. The method of claim 1, wherein the reacting of the THC-rich cannabinoid mixture with the benzoquinone reagent is at a temperature of between about 20° C. and about 190° C.

10. The method of claim 1, wherein the reacting of the THC-rich cannabinoid mixture with the benzoquinone reagent is at a temperature of between about 80° C. and about 120° C.

11. The method of claim 1, wherein the reacting of the THC-rich cannabinoid mixture with the benzoquinone reagent is in the presence of a solvent.

12. The method of claim 11, wherein the solvent is pentane, hexane, heptane, methanol, ethanol, isopropanol, dimethyl sulfoxide, acetone, ethyl acetate, diethyl ether, tert-butyl methyl ether, water, acetic acid, anisole, 1-butanol, 2-butanol, butane, butyl acetate, ethyl formate, formic acid, isobutyl acetate, isopropyl acetate, methyl acetate, 3-methyl-1-butanol, methylethyl ketone, 2-methyl-1-propanol, 1-pentanol, 1-propanol, propane, propyl acetate, trimethylamine, or a combination thereof.

13. The method of claim 1, wherein the CBN-rich cannabinoid mixture comprises at least about 60 wt. % CBN.

14. The method of claim 1, wherein the CBN-rich cannabinoid mixture comprises at least about 90 wt. % CBN.

15. The method of claim 1, wherein the benzoquinone reagent comprises:
 a compound as defined in formula (II) where $X^1$=H, $X^2$=C(CH$_3$)$_3$, $X^3$=C(CH$_3$)$_3$, and $X^4$=H,
 a compound as defined in formula (II) where $X^1$=Cl, $X^2$=Cl, $X^3$=Cl, and $X^4$=Cl,
 a compound as defined in formula (II) where $X^1$=H, $X^2$=C(CH$_3$)$_3$, $X^3$=H, and $X^4$=H,
 a compound as defined in formula (II) where $X^1$=H, $X^2$=C(CH$_3$)$_3$, $X^3$=H, and $X^4$=OCH$_3$, or
 a compound as defined in formula (II) where $X^1$=H, $X^2$=H, $X^3$=H, and $X^4$=OCH$_3$.

16. A method of converting tetrahydrocannabinol (THC) into cannabinol (CBN), the method comprising:

reacting the THC with a benzoquinone reagent that is a compound as defined in formula (II):

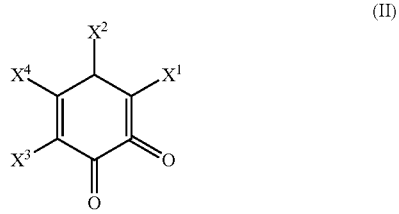

(II)

wherein $X^1$, $X^2$, $X^3$, and $X^4$ are each independently: H; a halide; a $C_{1-12}$-hydrocarbyl; a $C_{3-12}$-heteroaryl; a $C_{3-12}$-heteroaralkyl; a $C_{3-12}$-heteroaralkenyl; hydroxyl; a $C_{1-12}$-alkoxy; a $C_{0-12}$-amino; a $C_{1-12}$-acyl; a $C_{1-12}$-amide; a $C_{2-12}$-ester; or a $C_{2-12}$-ketone.

17. The method of claim 16, wherein the benzoquinone reagent comprises:
a compound as defined in formula (II) where $X^1$=H, $X^2$=C(CH$_3$)$_3$, $X^3$=C(CH$_3$)$_3$, and $X^4$=H,
a compound as defined in formula (II) where $X^1$=Cl, $X^2$=Cl, $X^3$=Cl, and $X^4$=Cl,
a compound as defined in formula (II) where $X^1$=H, $X^2$=C(CH$_3$)$_3$, $X^3$=H, and $X^4$=H,
a compound as defined in formula (II) where $X^1$=H, $X^2$=C(CH$_3$)$_3$, $X^3$=H, and $X^4$=OCH$_3$, or
a compound as defined in formula (II) where $X^1$=H, $X^2$=H, $X^3$=H, and $X^4$=OCH$_3$.

18. The method of claim 16, wherein the reacting of the THC with the benzoquinone reagent is in the presence of a solvent.

19. The method of claim 18, wherein the solvent is pentane, hexane, heptane, methanol, ethanol, isopropanol, dimethyl sulfoxide, acetone, ethyl acetate, diethyl ether, tert-butyl methyl ether, water, acetic acid, anisole, 1-butanol, 2-butanol, butane, butyl acetate, ethyl formate, formic acid, isobutyl acetate, isopropyl acetate, methyl acetate, 3-methyl-1-butanol, methylethyl ketone, 2-methyl-1-propanol, 1-pentanol, 1-propanol, propane, propyl acetate, trimethylamine, or a combination thereof.

* * * * *